United States Patent
Norman et al.

(10) Patent No.: US 10,617,753 B2
(45) Date of Patent: Apr. 14, 2020

(54) REMOVAL OF RESIDUAL CELL CULTURE IMPURITIES

(71) Applicant: NOVARTIS AG, Basel (CH)

(72) Inventors: Carnley Norman, Cambridge, MA (US); Eric Suda, Cambridge, MA (US); Kayla Dowless, Cambridge, MA (US); Ruiz Astigarraga, Cambridge, MA (US); Patrick Bastek, Cambridge, MA (US); Vaishali Yannone, Cambridge, MA (US)

(73) Assignee: NOVARTIS AG, Basel (CH)

( * ) Notice: Subject to any disclaimer, the term of this patent is extended or adjusted under 35 U.S.C. 154(b) by 0 days.

(21) Appl. No.: 16/136,953

(22) Filed: Sep. 20, 2018

(65) Prior Publication Data

US 2019/0083603 A1    Mar. 21, 2019

Related U.S. Application Data

(63) Continuation of application No. 15/035,302, filed as application No. PCT/EP2014/073986 on Nov. 6, 2014, now abandoned.

(60) Provisional application No. 61/904,747, filed on Nov. 15, 2013.

(51) Int. Cl.
| | |
|---|---|
| A61K 39/145 | (2006.01) |
| A61K 39/12 | (2006.01) |
| C07K 1/18 | (2006.01) |
| C12N 7/00 | (2006.01) |
| A61K 39/00 | (2006.01) |

(52) U.S. Cl.
CPC ............ *A61K 39/145* (2013.01); *A61K 39/12* (2013.01); *C07K 1/18* (2013.01); *C12N 7/00* (2013.01); *A61K 2039/53* (2013.01); *C12N 2760/16134* (2013.01); *C12N 2760/16151* (2013.01)

(58) Field of Classification Search
None
See application file for complete search history.

(56) References Cited

U.S. PATENT DOCUMENTS

| | | |
|---|---|---|
| 5,948,410 A | 9/1999 | Van Scharrenburg et al. |
| 2011/0165676 A1 | 7/2011 | Hopkins |
| 2011/0217330 A1 | 9/2011 | Andre et al. |
| 2012/0101262 A1 | 4/2012 | Arunakumari |
| 2014/0315277 A1 | 10/2014 | Andre et al. |
| 2016/0287693 A1 | 10/2016 | Norman |
| 2019/0083603 A1* | 3/2019 | Norman .................. C07K 1/18 |

FOREIGN PATENT DOCUMENTS

| | | |
|---|---|---|
| CN | 1477973 A | 2/2004 |
| EP | 0 870 508 | 10/1998 |
| WO | 2002/028426 A1 | 4/2002 |
| WO | 2007/052163 A2 | 5/2007 |
| WO | 2010/052214 | 5/2010 |
| WO | 2010151632 | 12/2010 |
| WO | 2011/154976 A1 | 12/2011 |

OTHER PUBLICATIONS

Onions, et al., Biologicals. (2010) 38:544-551.
International Search Report and Written Opinion dated Dec. 10, 2014, issued in International Application PCT/EP2014/073986.
Pamela Stanley, et al., The Polypeptide of Influenza Virus VIII. Large-Scale Purification of the Hemagglutinin, Virology (1973) 56:640-645.

* cited by examiner

*Primary Examiner* — Shanon A. Foley
(74) *Attorney, Agent, or Firm* — Duane Morris LLP; Thomas J. Kowalski; Mark W. Russell

(57) ABSTRACT

The present application discloses methods for removing residual impurities from protein preparations. Such methods include addition of an anionic detergent to a solution comprising proteins of interest and cellular contaminants under non-precipitating conditions and passing the solution through an ion exchange column.

20 Claims, 5 Drawing Sheets

REMOVAL OF RESIDUAL CELL CULTURE IMPURITIES

RELATED APPLICATIONS

The present application is a continuation of U.S. application Ser. No. 15/035,302, filed May 9, 2016, which is a § 371 of International Patent Application No. PCT/EP2014/073986, which was filed on Nov. 6, 2014, and published as PCT Publication No. WO 2015/071177 on May 21, 2015 and which claims the benefit of priority to U.S. Provisional Application Ser. No. 61/904,747 filed Nov. 15, 2013. The content of each of the aforementioned patent applications is incorporated herein in its entirety.

FIELD OF THE INVENTION

This invention relates to production of proteins in host cells and improved purification methods thereof.

BACKGROUND OF THE INVENTION

Various methods for producing vaccines and other biologics in cell cultures have been pre-described. If continuous cell lines are used for the production, there is the risk that residual DNA of the cell line could be oncogenic. It is therefore required to destroy and remove residual DNA from therapeutic proteins of interests. For viral vaccines the FDA currently recommends a DNA amount of less than 10 ng/dose and a fragment size of less than 200 base pairs (Guidance of Industry. Characterization and Qualification of Cell Substrates and other Biological Materials Used in the Production of Viral Vaccines for Infections Disease Indications. FDA/CBER February 2010; downloadable under: fda.gov/downloads/biologicsbloodvaccines/guidancecompliance regulatoryinformation/guidances/vaccines/ucm202439.pdf).

Several methods for removing residual DNA from cell culture derived vaccines have been described. U.S. Pat. No. 5,948,410 describes a method for producing flu vaccines derived from cell culture in which a DNAse treatment is combined with a splitting step using CTAB. WO 2007/052163 describes a method for producing flu vaccines derived from cell culture in which beta propiolactone (BPL) is used to inactive the virus and to degrade the residual DNA. Afterwards, the virus is split, e.g., by treatment with CTAB. The fragmented DNA is then removed from the virus preparation. Nevertheless, there is still the need to further improve removal of residual cellular DNA from influenza virus preparation or from other products of interest produced in continuous cell lines.

The use of caprylic acid in combination with ion exchange chromatography for the removal of cellular DNA from antibodies produced in cell culture has been disclosed in US 2012-0101262. However, US 2012-0101262 requires the use of caprylic acid under conditions that induce precipitation of residual DNA and contaminating proteins (in particular at low pH). Afterwards, the precipitate and the protein of interest can be separated, and the latter is further purified via ion exchange chromatography.

Various other methods of removing impurities and aggregates derived from cell cultures using caprylic acid or caprylate salts have been described in the art. Steinbuch (Steinbuch, M. et al. Arch. Biochem. Biophys. 134:279-94 (1969) describes recovering IgG from human plasma by caprylate precipitation of nonenveloped and enveloped viruses therein. U.S. Pat. No. 7,553,938 describes purification of antibodies from a starting solution by adding caprylate or heptanoate ions at pH 4.6 to about 4.95 and filtering the solution through at least one anion exchange resin. U.S. Pat. No. 5,886,154 describes a process for purification of antibodies from human plasma involving suspension of antibodies at pH 3.8 to 4.5 followed by addition of caprylic acid at pH 5.0 to 5.2 to precipitate contaminating proteins and lipids while the antibodies remain in solution. The use of caprylic acid is employed in antibody purification because short fatty acids form insoluble complexes with alpha and beta globulins and at acidic pH whereas the gamma globulins are not as readily precipitated (Chanutin et. al., 1960). Thus the gamma globulin can easily be separated. Yet, none of these disclosures teach or suggest using an anionic detergent to remove residual DNA from viral proteins under conditions which prevent precipitation as taught herein.

SUMMARY OF THE INVENTION

The present invention relates to manufacturing of proteins and improved purification methods thereof. In particular, the invention provides methods for removing cellular contaminants, such as residual nucleic acids, from protein products produced in a suitable host (e.g., host cells). Accordingly, the invention also encompasses related compositions prepared by such methods.

The invention thus includes methods, which increase the yield, purity and/or safety of biological products produced from cell culture. Biological products prepared by methods of the invention may include, but are not limited to: biopharmaceuticals, proteins, polysaccharides, viral antigens, and antibodies. In a particular aspect, the method provides a biological product substantially free of residual DNA.

The inventors have surprisingly found that purification of sample comprising protein and DNA derived from cell culture is significantly improved by an addition of an anionic detergent to a solution comprising the proteins and cellular DNA, followed by a purification step comprising an ion exchange matrix. The problem to be solved might relate to the inefficiency of separation of negatively charged DNA impurities from proteins of interest on a positively charged ion exchange matrix. It can be assumed that secondary interactions were playing a role in the diminished ability of anion exchange chromatography to adsorb the negatively charged DNA impurity. The present invention now achieves an enriched product and increased yield thereof, by contacting residual DNA with an anionic detergent solution and processing the residual DNA by adsorption over an anion exchange matrix. The inventors have unexpectedly found that the present invention also removes influenza nucleoproteins. Efficient removal of contaminants as achieved by the present invention allows higher yields of product, because incubation and infection times can be increased so that a higher amount of the protein of interest can be obtained. The invention also encompasses the recognition that a particularly effective removal of residual DNA from influenza viruses produced in cell culture can be achieved, if the virus preparation is purified via an ion exchange chromatography in the presence of an anionic detergent, such as fatty acid detergents (e.g., sodium caprylate).

Surprisingly, the inventors have also found the process described herein substantially removes the influenza Nucleoprotein (NP). Advantageously, the invention is not restricted to influenza virus derived from cell culture, but is also applicable to influenza viruses produced in eggs, if removal of NP is desired.

Unlike methods described in prior art (see the "Background" above), the present invention employs an anionic detergent under conditions that do not precipitate the proteins of interest or DNA. According to the invention, the preparation of the protein of interest is separated from contaminating DNA/proteins through ion exchange chromatography. By using the process described herein, the amount of impurities (e.g., residual DNA) in the sample can be dramatically reduced. This invention can be used to remove residual cellular DNA from any samples containing one or more proteins of interest produced in host cells, such as cell culture.

Accordingly, the present invention provides a method for removing residual cellular DNA from a sample comprising a protein of interest produced in host cells, such as cell cultures, comprising adding an anionic detergent to a solution comprising the protein of interest under non-precipitating conditions and passing the solution through an ion exchange matrix to remove residual cellular DNA. The methods of the invention are not limited by a particular protein of interest. Non-limiting examples of proteins that can be purified in accordance with the present invention include, but are not limited to: therapeutic proteins, antigens (e.g., immunogenic proteins), antibodies or fragments thereof.

According to the invention, a suitable starting material which can be subjected to the methods provided herein may be a solution comprising a protein of interest. Such solution may be a crude cell or tissue preparation, a partially purified preparation, culture media in which cells were grown, or cell culture supernatant, etc., but is likely to contain residual cellular contaminants desired to be removed.

The protein of interest may be grown in a suitable host cell system and can be purified or clarified from cell impurities by common separation techniques known in the art. Optionally, further steps may be taken prior to the passage of protein through the ion exchange matrix, preferably prior to the addition of the anionic detergent. For example the protein of interest may first be purified from cell culture impurities to produce a solution which has been clarified. The eluate or flow-through obtained from the method of the present invention can be subjected to further processing steps, such as purifying the protein of interest and formulating it into a vaccine. In some embodiments of the invention, the anionic detergent is added to the clarified solution by contacting the solution comprising the protein of interest and cell culture impurities with an anionic detergent solution under non-precipitating conditions and passing the solution through an ion exchange matrix. Non-precipitating conditions are conditions under which no substantial precipitation or proteins or DNA occurs.

Thus, the present invention is suitable for the production of viral proteins. Viral proteins of interest may be produced in a suitable host (such as cultured cells) infected with the virus. In some embodiments, the process of viral protein production may include splitting of virions, which typically involves the use of a splitting agent or another detergent. In some embodiments, the anionic detergent used in the methods described herein is not the splitting agent or the detergent used in the splitting process.

Alternatively or additionally, the invention provides a method for decreasing residual cellular DNA by passing a solution comprising proteins, cellular DNA in the presence of an anionic detergent through an ion exchange matrix under non-precipitating conditions and adsorbing substantially all of the cellular DNA on the ion exchange matrix. In a preferred aspect the anionic detergent is not the splitting agent or another detergent used in process. Further steps may be taken prior to the passage of proteins and cellular DNA through the ion exchange matrix, preferably prior to the addition of the anionic detergent. For example the virus may be split with a splitting agent and the proteins may be separated from cell culture debris comprising the split virus to produce a solution which has been clarified. The eluate or flow-through obtained from the ion exchange matrix produced by the present invention may be subjected to further processing steps such as further purifying the viral protein and formulating it into a vaccine.

The present invention is in particular applicable for the preparation of viral proteins for vaccine production. In another embodiment the present invention provides a method for removing residual cellular DNA from a sample comprising viral protein produced in cell culture, comprising adding an anionic detergent to a solution comprising the protein of interest under non-precipitating conditions, passing the solution through an ion exchange matrix, whereby the residual cellular DNA is bound to the ion exchange resin. In a preferred aspect the anionic detergent is not the splitting agent or another detergent used in process. Optionally further steps may be taken prior to passage through the ion exchange matrix, preferably prior to the addition of an anionic detergent. For example the virus may first be split with a splitting agent followed by separation of the split virus from cell culture debris to produce a solution which has been clarified. The eluate or flow-through obtained from the ion exchange matrix produced by the present invention may be subjected to further processing steps such as further purifying the viral protein and formulating it into a vaccine.

A particularly effective purification method for biological products derived from cell culture should make it possible to optimally remove impurities such as host cell DNA, while at the same time achieving a maximum yield of product. To this end, the present invention provides products substantially free of impurities and enriched for the immunogenic protein. According to the invention, residual DNA and impurities derived from host cells such as cell culture propagation may be removed from the intended product by passage in a solution comprising an anionic detergent, which is subsequently processed through an ion exchange matrix.

Accordingly, the present invention provides a method for preparing a vaccine composition comprising proteins of interest derived from a cell culture comprising adding a fatty acid detergent (as defined below) to a solution comprising proteins of interest under non-precipitating conditions and processing the protein of interest on an ion exchange matrix. The present invention may be useful for biopharmaceutical vaccine products.

In a preferred aspect, the invention provides a method for producing an influenza vaccine composition comprising immunogenic proteins derived from a virus derived from cell cultures comprising adding a fatty acid detergent to a solution comprising immunogenic proteins under non-precipitating conditions and processing the immunogenic proteins on an ion exchange matrix. The immunogenic proteins include hemagglutinin, neuraminidase, and nucleoproteins obtained from an influenza virus which has been subjected to inactivation and splitting agents. Additional steps may be taken prior to processing the immunogenic protein on the ion exchange matrix, preferably prior to the addition of a fatty acid detergent. For example the influenza virus may first be split with a splitting agent followed by separation of the split virus from cell culture debris to produce a solution which has been clarified. The eluate or flow-through obtained from the ion exchange matrix produced by the present invention may be subjected to further processing steps such as further purifying the viral protein and formulating it into a vaccine. In a preferred aspect the fatty acid detergent is not the splitting agent or another detergent used in process.

As mentioned above, the present invention also encompasses the surprising finding that the process described herein substantially removes influenza nucleoprotein (NP). Advantageously, the invention is not restricted to influenza virus derived from cell culture, but is also applicable to influenza viruses produced in eggs, if removal of NP is desired.

Thus, the invention provides a method for removing viral nucleoproteins from viral proteins of interest. An anionic detergent is added to a solution comprising viral nucleoproteins under non-precipitating conditions. In some embodiments, the anionic detergent is not the splitting agent or another detergent used in process. The nucleoproteins can then be bound to an ion exchange matrix to produce an eluate (or flow-through) comprising the proteins of interest which are substantially free of viral nucleoproteins and cellular DNA. In some embodiments, a suitable anionic detergent solution used for the present invention does not include deoxycholate, sodium lauryl sulfate, or combination thereof.

Accordingly the present invention provides a method for removing influenza nucleoproteins from an influenza virus preparation derived from cell culture or embryonated eggs comprising adding a anionic detergent to the virus preparation under non-precipitating conditions, and processing the virus preparation through an anion exchange matrix, whereby the nucleoprotein is bound to the anion exchange matrix. Additional steps may be taken prior to processing the virus preparation on the ion exchange matrix, preferably prior to the addition of an anionic detergent. For example the influenza virus may first be split with a splitting agent followed by separation of the split virus from cell culture debris to produce a solution which has been clarified. The eluate or flow-through obtained from the ion exchange matrix produced by the present invention may be subjected to further processing steps such as further purifying the viral protein and formulating it into a vaccine. In a preferred aspect the anionic detergent is not the splitting agent or another detergent used in process.

The present invention provides an influenza vaccine produced by the method of the present invention which is substantially free of residual DNA, and nucleoprotein. The influenza vaccine can be formulated in a subvirion particle form, for example HA and NA proteins may be purified subunit proteins or bound to portions of influenza viral structures.

DETAILED DESCRIPTION OF CERTAIN EMBODIMENTS

Protein of Interest

Figure 1:
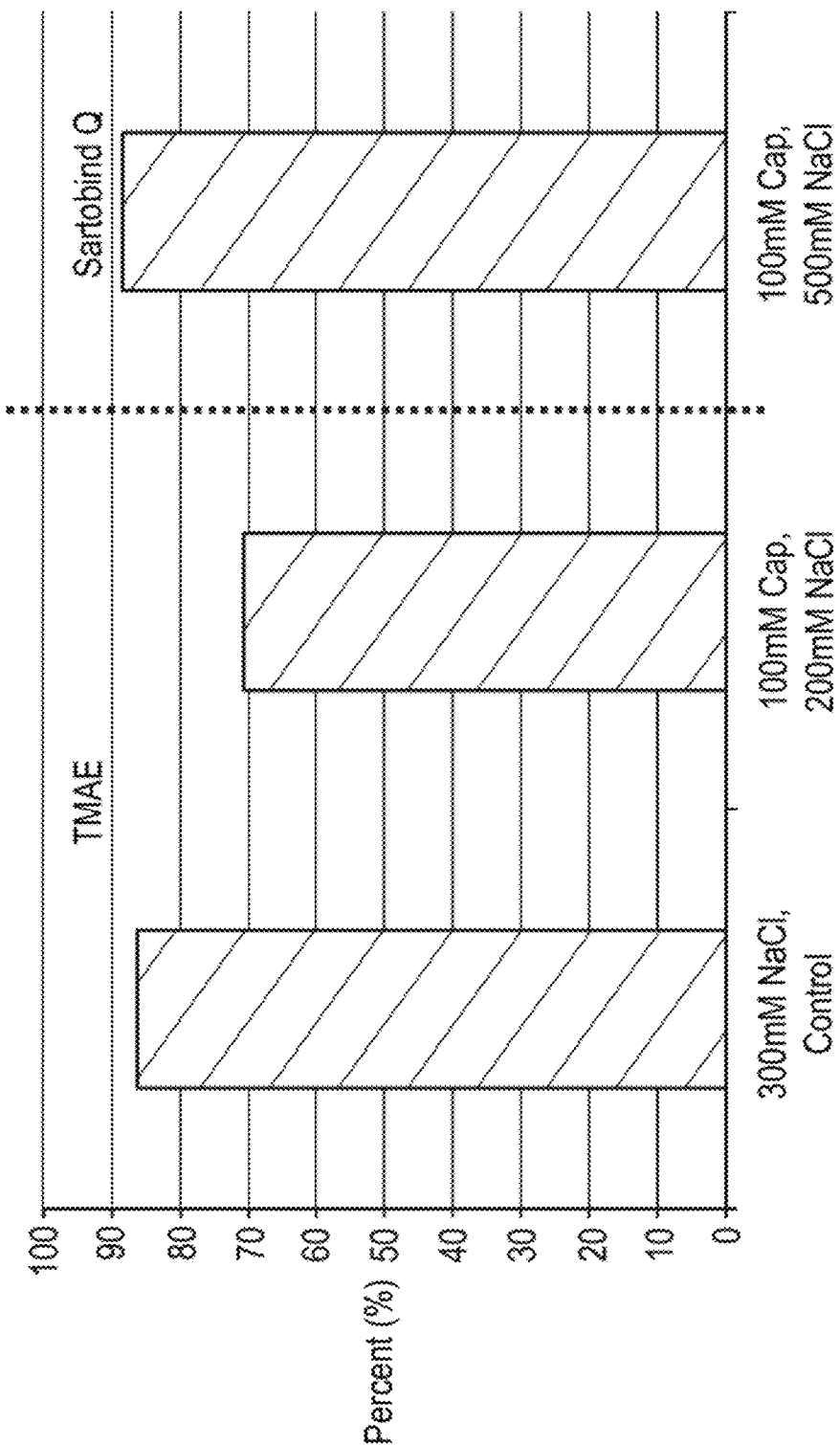
FIG. 1 provides a bar graph comparing percent yield of HA protein processed on TMAE and SARTOBIND Q using different chaotropic agents.

The methods of the invention can be used to purify any protein of interest derived from a host cell source (such as cell cultures) from residual host cell contaminations, such as cellular DNA. Modern virus production methods as described here have much in common with bioprocessing of recombinant protein or monoclonal antibody production. Thus, in a particular aspect, the methods are employed to purify proteins of interest, e.g., therapeutic proteins, immunogenic proteins or antigens, antibodies or fragments thereof, generated in host cells, such as eukaryotic (e.g., mammalian, avian, insect, plant, fungal, etc.) cell cultures and prokaryotic (e.g., bacterial) cell cultures, cell lysates thereof, clarified bulk (e.g., clarified cell culture supernatant), or animal derived protein mixtures or extracts.

In certain embodiments, the methods comprise effectively removing host cell contaminants (e.g., impurities) from a mixture (host cell-derived preparation, e.g., a cell culture, cell lysate, clarified bulk, etc.) containing one or more proteins of interest. In some embodiments, suitable starting materials for the methods described herein include host cell-derived preparations (such as sample solutions and cell lysates) comprising one or more proteins of interest and residual host cell contaminants in an amount that is undesirable for intended purposes. In some embodiments, such starting materials are crude cell lysates. In some embodiments, such starting materials are cell culture supernatants comprising secreted proteins (for example, cell culture media in which host cells are grown). In some embodiments, such starting materials are presented as a partially purified form.

Thus one aspect of the present invention provides a method for removing residual cellular DNA from a sample comprising a protein of interest produced in a suitable system, such as cell culture, comprising steps of adding at least one anionic detergent to a solution comprising the protein of interest under non-precipitating conditions; passing the solution through an ion exchange matrix, whereby the residual cellular DNA is bound to the ion exchange resin, so as to separate the protein of interest from the residual DNA (e.g., in an eluate or flow-through); and, optionally, further purifying the protein of interest and formulating it into a product. In some embodiments, the resulting purified protein of interest is suitable for use in the manufacture of pharmaceutical compositions. Thus, such protein or proteins may be formulated as a pharmaceutical product, such as biologic therapeutics and vaccines.

Accordingly, the methods described herein are useful for the preparation of viral proteins produced in a suitable host. In some embodiments, such viral proteins are viral immunogenic proteins (i.e., viral antigens) suitable for vaccine production.

Immunogenic proteins suitable for use in the invention may be derived from any virus which is the target of a vaccine. The immunogenic proteins may be formulated as inactivated (or killed) virus, attenuated virus, split virus formulations, purified subunit formulations, viral proteins which are isolated, purified or derived from a virus, and virus like particles (VLPs).

If during vaccine production, a splitting step is to be used, the splitting agent may be different from the anionic detergent of the methods described herein. Preferably the splitting step or splitting agent is added prior to the ion exchange chromatography on which the residual cellular DNA is bound or separated from the protein of interest.

The immunogenic proteins of the invention are viral antigens which preferably include epitopes which are exposed on the surface of the virus during at least one stage of its life cycle. Viruses may be non-enveloped or, preferably, enveloped. Viruses are preferably RNA viruses, and more preferably ssRNA viruses. They may have a sense or, preferably, an antisense genome. Their genomes may be non-segmented or, preferably, segmented. Preferred viruses of the invention include influenza virus comprising viral antigens such as neuraminidase (NA) and hemagglutinin (HA) proteins.

Virus Culture

The invention provides a method of preparing an influenza virus, and removal of residual DNA or impurities generated during the processing of a viral antigens for vaccine production. Accordingly, the invention provides a method for removing nucleoproteins from an influenza virus preparation. Influenza virus may be cultured in a host and purification steps taken to isolate and purify NA and HA proteins. Thus in one aspect of the present invention relates to a method for removing Influenza Nuclear Protein (NP) from a preparation comprising virus proteins of interest, comprising splitting a virus preparation obtained from cell culture or eggs, contacting the virus preparation with a anionic surfactant under non-precipitating conditions and processing the preparation through an ion exchange matrix, whereby the nuclear protein is bound to the anion exchange resin, and optionally further purifying the viral protein and formulating it into a vaccine.

The culture host may be cells or embryonated hen eggs, which are suitable for producing a vaccine that can be used for administration to humans. Non-limiting examples of suitable cells which have been approved for vaccine manufacture include MDCK cells, CHO cells, Vero cells and PER.C6® cells. For the embodiments of the inventions involving the use of eggs, the viruses may also be propagated in eggs. The current standard method for influenza virus growth for vaccines uses embryonated SPF hen eggs, with virus being purified from the egg contents (allantoic fluid). It is also possible to passage a virus through eggs and subsequently propagate it in cell culture and vice versa. Methods for purification of vaccine products cultivated in embryonated eggs is described, for example, in GB 1498261.

Preferably, the cells are cultured in the absence of serum, to avoid a common source of contaminants. Various serum-free media for eukaryotic cell culture are known to the person skilled in the art, e.g., Iscove's medium, ultra CHO medium (BioWhittaker), EX-CELL (JRH Biosciences). Furthermore, protein-free media may be used, e.g., PF-CHO (JRH Biosciences). Otherwise, the cells for replication can also be cultured in the customary serum-containing media (e.g., MEM or DMEM medium with 0.5% to 10% of fetal calf serum).

Virus may be grown on cells in adherent culture or in suspension. Microcarrier cultures can be used. In some embodiments, the cells may thus be adapted for growth in suspension. The suspension may first be clarified using any method known in the art. The clarification step serves to remove cells, cell debris, and host cell impurities from the sample. In some embodiments, clarification may be performed via one or more centrifugation steps. Centrifugation of the sample may be performed by routine methods known in the art. For example, centrifugation may be performed using a normalized loading of about $1 \times 10^{-8}$ m/s and a gravitational force of about 5,000×g to about 15,000×g.

Purification

In another aspect, the suspension may be clarified via one or more depth filtration techniques. Depth filtration refers to a method of removing particles from solution using a series of filters, arranged in sequence, which have decreasing pore size. A depth filter three-dimensional matrix creates a maze-like path through which the sample passes. The principle retention mechanisms of depth filters rely on random adsorption and mechanical entrapment throughout the depth of the matrix. In various aspects, the filter membranes or sheets may be wound cotton, polypropylene, rayon cellulose, fiberglass, sintered metal, porcelain, diatomaceous earth, or other known components. In certain aspects, compositions that comprise the depth filter membranes may be chemically treated to confer an electropositive charge, i.e., a cationic charge, to enable the filter to capture negatively charged particles, such as DNA, host cell proteins, or aggregates.

The methods according to the invention also include harvesting and isolation of viruses or the proteins generated from cell culture. During isolation of viruses or proteins, the cells are separated from the culture medium by standard methods such as separation, filtration or ultrafiltration. The viruses or the proteins are then concentrated according to methods sufficiently known to those skilled in the art, such as gradient centrifugation, filtration, precipitation, chromatography, etc., and then purified. It is also preferred according to the invention that the viruses are inactivated during or after purification. Virus inactivation can occur, for example, by β-propiolactone or formaldehyde at any point within the purification process.

Any depth filtration system available to one of skill in the art may be used throughout the steps of present invention. In a particular embodiment, clarification and purification by depth filtration may be accomplished with a MILLISTAK+ Pod depth filter system, X0HC media, available from Millipore Corporation. In another aspect, the depth filtration step may be accomplished with a ZETA PLUS Depth Filter, available from 3M Purification Inc.

Vaccine Production

Vaccines are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccines. It is particularly suitable for manufacturing influenza vaccines, however, which generally comprise residual DNA and nucleoprotein in a detectable amount. Such influenza vaccines include live virus, whole virion or split virion influenza vaccines. Where the vaccine is formulated in a subvirion form, the viral antigens can be found in a split virus form, where the viral lipid envelope has been dissolved or disrupted, or in the form of one or more purified viral proteins.

As a further alternative, the vaccine may include a whole virus, e.g., a live attenuated whole virus, an inactivated whole virus, etc. Methods for inactivating or killing viruses to destroy their ability to infect mammalian cells are known in the art. Such methods include both chemical and physical means. Chemical means for inactivating a virus include treatment with an effective amount of one or more of the following agents: detergents, formaldehyde, formalin, BPL, and UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. Preferably, the virus is inactivated with BPL.

Figure 5:
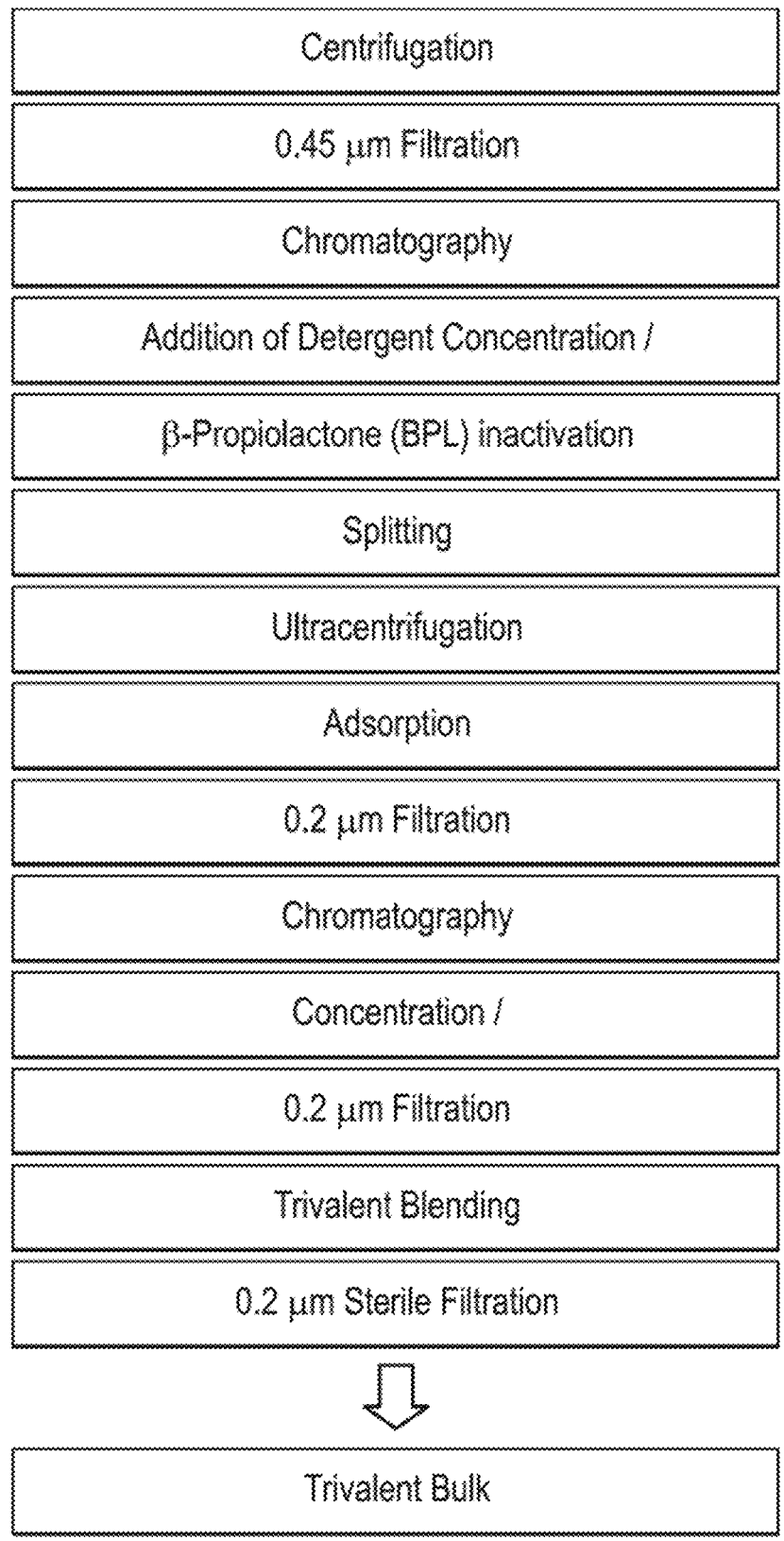
FIG. 5 provides the downstream process for obtaining a cell culture based subunit influenza vaccine, as described in Onions et al., 2010.

Residual DNA may be inactivated with an alkylating agent that cleaves the DNA into portions small enough so that it is unable to code for a functional protein. Preferably, the length of degraded residual cell culture DNA is less than 500 base pairs. More preferably, the length of degraded residual cell culture DNA is less than 200 base pairs. Preferably, the use of an alkylating agent such as betapropiolactone (BPL) in the invention provides the additional benefit of reducing aggregation and contaminants. Vaccine formulations with reduced aggregates may also have improved immunogenicity. US 2009-0304729 teaches the treatment of functional residual DNA with alkylating agents. Prior to the use of the anionic detergent in combination with ion exchange chromatography, parts of the fragmented residual DNA can be removed by precipitation with a cationic detergent like CTAB as described in Onions et al. (2010; Biologicals, 38(5): 544-551). The whole downstream process of Onions is shown in FIG. 5. In some embodiments, the present invention can be applied as part of the Onions process.

Methods of splitting viruses, such as influenza viruses, are well known in the art, e.g., see International Patent Publications: WO 02/28422, WO 02/067983, WO 02/074336, WO 01/21151, etc. Splitting of the virus is carried out by disrupting or fragmenting whole virus, whether infectious (wild-type or attenuated) or non-infectious (e.g., inactivated), with a disrupting concentration of a splitting agent. Splitting agents generally include agents capable of breaking up and dissolving lipid membranes, typically with a hydrophobic tail attached to a hydrophilic head. A preferred splitting agent is cetyltrimethylammoniumbromide (CTAB). The disruption results in a full or partial solubilization of the virus proteins, altering the integrity of the virus. Preferred splitting agents are non-ionic and ionic (e.g., cationic) surfactants, e.g., alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g., the Triton surfactants, such as Triton X-100 or Triton N101), polyoxyethylene sorbitan esters (the Tween surfactants), polyoxyethylene ethers, polyoxyethylene esters, etc.

One useful splitting procedure uses the consecutive effects of sodium deoxycholate and formaldehyde, and splitting can take place during initial virion purification (e.g., in a sucrose density gradient solution). Thus a splitting process can involve clarification of the virion-containing material (to remove non-virion material), concentration of the harvested virions (e.g., using an adsorption method, such as $CaHPO_4$ adsorption), separation of whole virions from non-virion material, splitting of virions using a splitting agent in a density gradient centrifugation step (e.g., using a sucrose gradient that contains a splitting agent such as sodium deoxycholate), and then filtration (e.g., ultrafiltration) to remove undesired materials. Split virions can usefully be resuspended in sodium phosphate-buffered isotonic sodium chloride solution.

A composition (such as a vaccine) that is "substantially free of residual DNA" refers to a composition or formulation, wherein residual DNA fragments of less than 200 basepairs are detectable at less than 10 ng per 0.5 ml, as determined by capillary electrophoresis (see, e.g., WO 2009/118420). The total amount of residual DNA in compositions of the invention is preferably less than 20 ng/ml, e.g., ≤10 ng/ml, ≤5 ng/ml, ≤1 ng/ml, ≤100 pg/ml, ≤10 pg/ml, etc.

Accordingly, an assay used to measure residual DNA will typically be a validated assay (Guidance for Industry: Bioanalytical Method Validation. U.S. Department of Health and Human Services Food and Drug Administration Center for Drug Evaluation and Research (CDER) Center for Veterinary Medicine (CVM). May 2001; Lundblad (2001) Biotechnology and Applied Biochemistry 34:195-197). Three principle techniques for DNA quantification can be used: hybridization methods, such as Southern blots or slot blots (Ji et al. (2002) Biotechniques. 32:1162-7); immunoassay methods, such as the THRESHOLD System (Briggs (1991) J Parenter Sci Technol. 45:7-12; and quantitative PCR (Lahijani et al. (1998) Hum Gene Ther. 9:1173-80). These methods are all familiar to the skilled person, although the precise characteristics of each method may depend on various factors such as choice of probes for hybridization, the choice of primers and/or probes for amplification, etc.

In another aspect, the invention provides methods for preparing influenza vaccine compositions which have reduced levels of nucleoproteins (NP). Preferably, NP makes up less than 15% by mass of the total influenza virus protein in the vaccine, e.g., <12%, <10%, <8%, <7%, <6%, <5%, <4%, <3%, <2%, or <1%. The vaccine may comprise less than 3 µg NP per 10 µg of HA, less than 2.5 µg NP per 10 µg of HA, less than 2 µg NP per 10 µg of HA, less than 1.5 µg NP per 10 µg of HA, less than 1 µg NP per 10 µg of HA, less than 0.5 µg NP per 10 µg of HA or less than 0.1 µg NP per 10 µg of HA. Most preferably, the vaccine is substantially free of NP. This is understood as having less than 0.1 µg NP per 10 µg of HA. In some embodiments, the methods provided herein may achieve at least 10-fold reduction in the amount of NP in a preparation, e.g., at least 10-fold, at least 12-fold, at least 15-fold, at least 20-fold, at least 25-fold, at least 30-fold, at least 40-fold, at least 50-fold, at least 75-fold, or at least 100-fold reduction in the amount of NP in a flow-through (or eluate) as compared to the starting material subjected to the purification methods of the invention.

Methods to determine the amount of protein in a composition are known to the skilled person in the art. However, since NP and NA have virtually the same molecular weight (around 60 kD), they usually co-migrate in non-reducing gels. Classic SDS gel-electrophoresis might therefore not be an appropriate way to determine the amount of NP (see Chaloupka et al., 1996, Eur J Clin Microbiol Infect Dis. 1996 February; 15(2):121-7.). One way to determine the amount of NP in a vaccine bulk might be a 2 dimensional electrophoresis with a subsequent densitometry. Preferred, however is isotope dilution mass spectrometry using an isotopically labeled synthetic peptide as described, for example, in: Williams et al., Vaccine 30 (2012) 2475-2482. Such method uses liquid chromatography—tandem mass spectrometry (LC-MS/MS) using isotope dilution in conjunction with multiple reaction monitoring (MRM). This method quantifies targeted peptides released by proteolytic digestion of the sample as a stoichiometric representative of the analyte protein. A stable isotope-labeled reference peptide is spiked into the sample as an internal standard (IS).

Quantification of NP is achieved by comparing the peak area of the isotopically labeled reference peptide with that of the endogenous target peptide. This method allows simultaneous quantification of multiple proteins, provided labeled peptides are included for each specific target.

Alternatively, label free mass spectrometry (LC/MSE) is used for the quantification, preferably in quadrupole time-of-flight (Q-Tof) mass spectrometers (Getie-Kebtie et al., (2013): Influenza and Other Respiratory Viruses 7(4), 521-530). For this method, alternating scans of low collision energy and elevated collision energy during LC/MS analysis are used to obtain both protein identity and quantity in a single experiment. Quantification is based on the experimental data showing that the average signal intensity measured by LC/MSE of the three most intense tryptic peptides for any given protein is constant at a given concentration, regardless of protein type and size. As the signal intensity is proportional to concentration, the amount of any protein in the mixture can be estimated.

The present invention also includes influenza vaccines based on viruses grown in cell culture (preferably mammalian or avian cells), whereby the vaccines have an amount of residual cellular DNA of less than 5 ng/dose (e.g., less than 4 ng, less than 3 ng, less than 2 ng or less than 1 ng per dose) at a fragment size of less than 200 base pairs, and whereby the vaccine contains less than 1 µg NP per 10 µg of HA, less than 0.5 µg NP per 10 µg of HA, or less than 0.1 µg NP per 10 µg of HA. Most preferably, the vaccine is substantially free of NP. This is understood as having less than 0.1 µg NP per 10 µg of HA. In particular the influenza vaccine is contains less than 1 ng residual DNA per dose at a fragment size of less than 200 base and less than 0.5 µg NP per 10 µg of HA. This vaccine is most preferably free from mercury-containing preservatives and antibiotics. The vaccine is most preferably a tetravalent seasonal or monovalent pandemic influenza vaccine with an amount of residual cellular DNA of less than 1 ng per dose at a fragment size of less than 200 base pairs and less than 0.5 µg NP per 10 µg of HA.

Such vaccine preparations can be obtained, for example, by the following process, which is a particularly preferred embodiment: A method for producing an influenza virus vaccine in which the following steps are conducted: Influenza viruses are grown in cell culture, e.g., in MDCK suspension cells (WO 1997/037000). The viruses are harvested, purified and concentrated by 0.45 micrometer filtration and CS chromatography. After addition of detergent (such as polysorbates, e.g., Tween® 80), the virus preparation is treated with BPL. Afterwards the viruses are split with CTAB. After an ultracentrifugation and adsorption step the viral protein preparation is subject to ion exchange chromatography, using TMAE or Sartobind Q as a resin. The chromatography is done in the presence of sodium caprylate (about 50 mM for Sartobind; 100 mM for TMAE) and sodium chloride (400 mM for Sartobind), and 200 mM for TMAE). Afterwards the protein preparation is concentrated by a suitable means, such as ultrafiltration. The proteins might be optionally blended with other virus preparation (in the case of tri- or tetravalent seasonal vaccines), and optionally sterile filtrated, filled and packaged. The invention thus includes influenza vaccine obtainable by this process.

It will be evident to the artisan that the measure of the residual host cell DNA content is not meant as a limitation or defining feature of this methodology. Instead, these data in the examples support the essence of the present invention: a large-scale methodology for the generation of virus particles that results in a highly purified product that may be utilized in clinical and commercial settings. It can be noted that the importance of achieving particular DNA levels in the final product is product-specific. Viral products produced using continuous cell lines for parenteral use in humans will require the most stringent purity standards but, even in that case, the goals may vary from 100 pg per dose up to 10 ng per dose (WHO Requirements for the Use of Animal Cells as in vitro Substrates for the Production of Biologicals Requirements for Biological Substances No. 50), WHO Technical Report Series, No. 878, 1998) or higher, and are likely to be adjusted depending on the product's indication.

Detergents

The anionic detergents used in the present invention are detergents which are added as an extra substance for carrying out ion exchange. Accordingly, the detergent itself is not removed by the ion exchange process nor precipitates the substances processed through the matrix but serves to interact with the hydrophobic regions of the residual DNA and/or the virus or viral proteins, particularly the HA subunit. In some embodiments, the anionic detergent used for the present invention excludes deoxycholate and/or sodium lauryl sulfate.

In preferred embodiments, one or more anionic detergents are used. In preferred embodiments, fatty acid detergents are used (as defined below). In particularly preferred embodiments, eight-carbon fatty acids are used. For example, in some embodiments, caprylic acids (e.g., sodium caprylate) are used.

In one aspect, an anionic detergent solution is added to a solution having the proteins of interest. If used for viral preparations, the anionic detergent is preferably added following inactivation or splitting of viruses, whereby inactivation may be performed before or after splitting steps. In one aspect, the anionic detergent, is added during or prior to an ion exchange step. The addition of a anionic detergent significantly improves clearance of residual DNA by at least 10%, 20%, 30%, 40% or 50%, as compared to clearance of residual DNA without treatment. List of commercially available anionic detergents can be found, e.g., under: signaaldrich.com/life-science/biochemicals/biochemical-product-s.html?-TablePage=14572921.

Preferred anionic detergents are cholates, deoxycholates, 1-decanesulfonates, and lauryl sulfate. Other suitable detergents include cetylpyridinium bromide, alkyl benzyldimethylammonium chloride, tetradecyltrimethylammonium chloride, hexadecylammonium chloride, and orinthinyl-cysteinyl-tetradecylamide.

Figure 2:
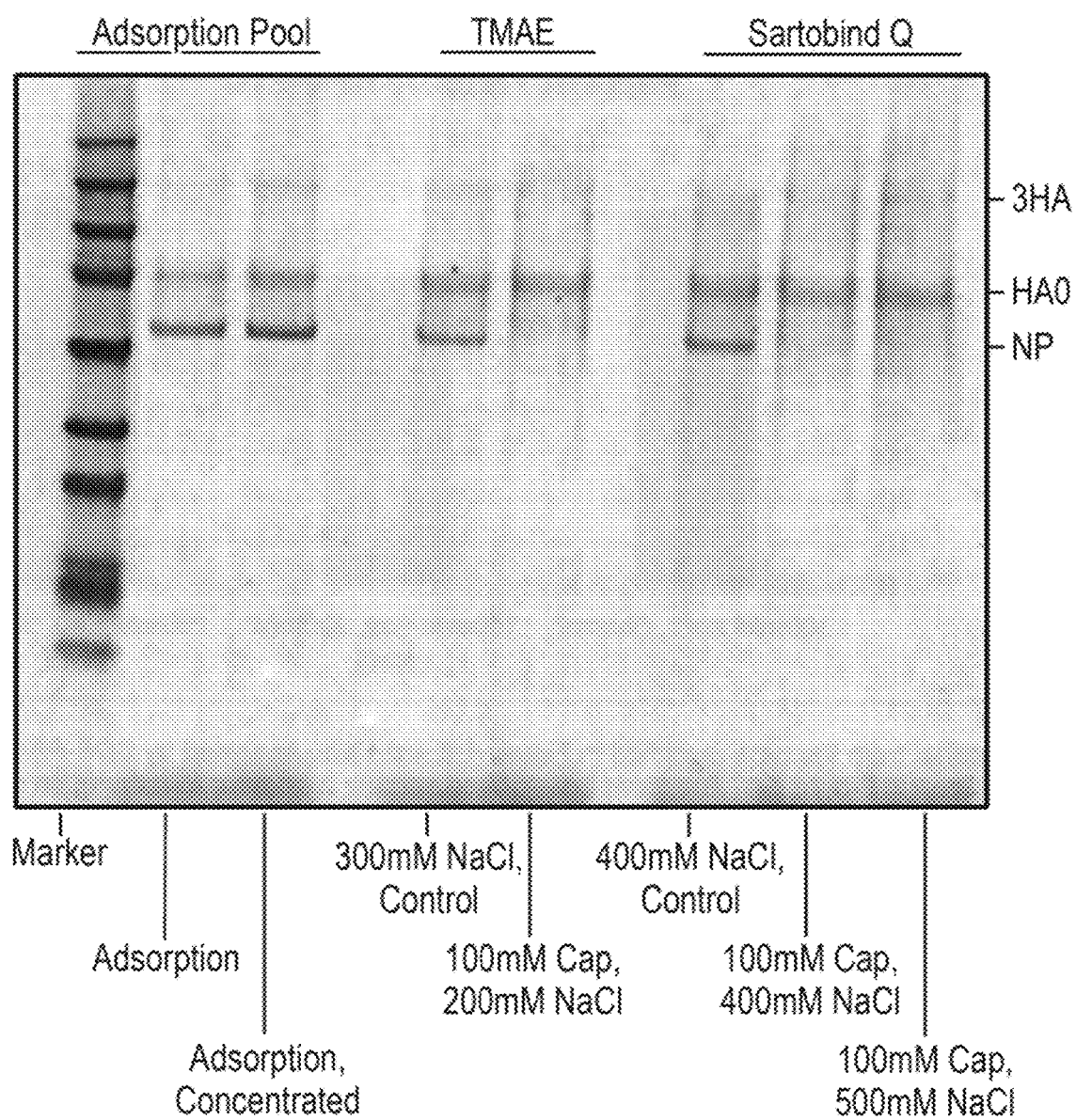
FIG. 2 provides a denaturing gel comparing samples from chromatography runs with and without capryliate as a detergent.
Figure 3:
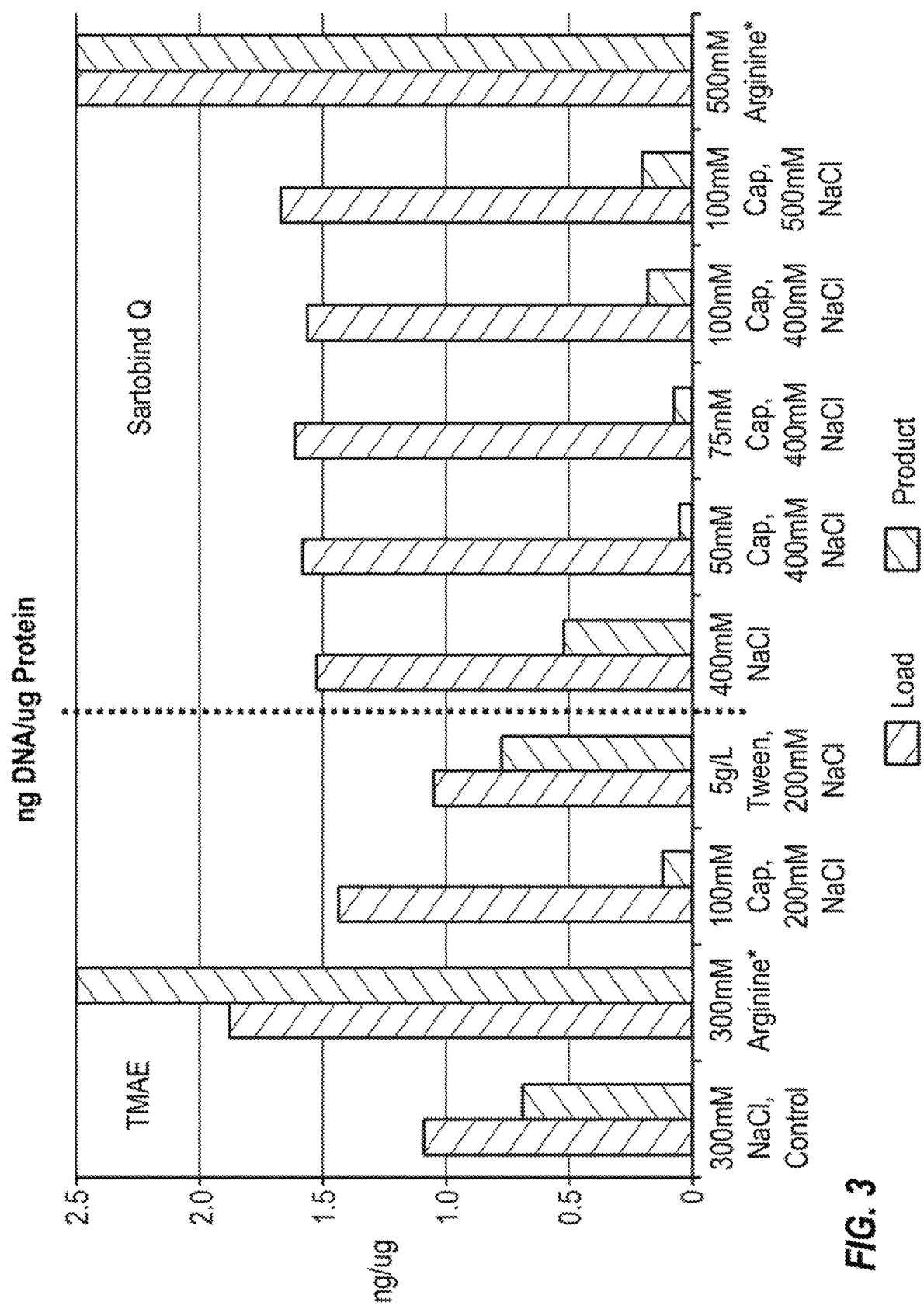
FIG. 3 provides a bar graph comparing ratio of DNA/protein recovered from ion exchange matrices run with different amounts of caprylate.
Figure 4:
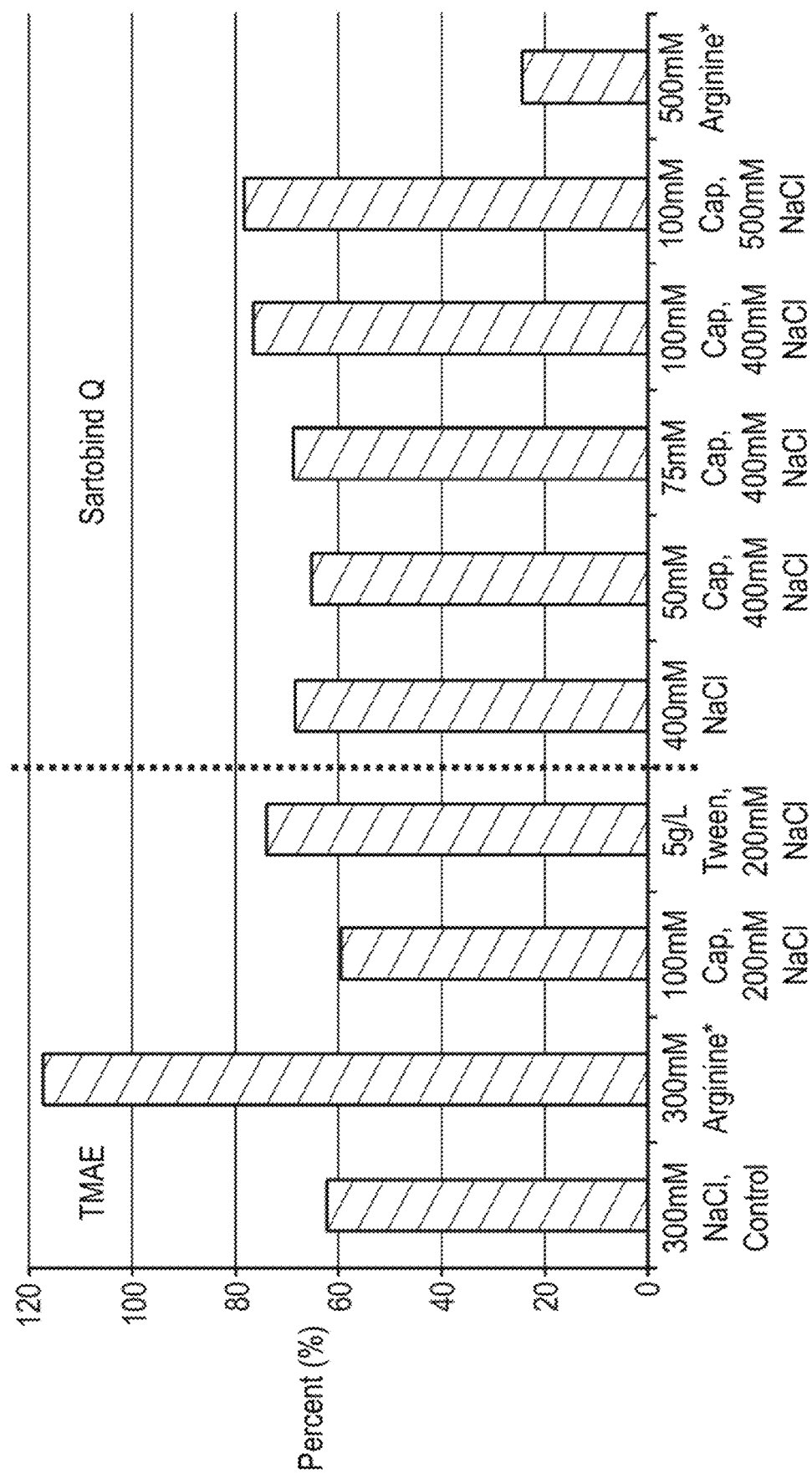
FIG. 4 provides percent yield of protein recovered from ion exchange matrices run with different amounts of caprylate.

In some embodiments, suitable anionic detergents are fatty acid detergents. In the context of the present disclosure, fatty acid detergents are understood to be salts of fatty acid, particularly carboxylic fatty acids selected from C4-C18 carbon chains, preferably C6-C10 carbon chains, e.g., C6, C8 and C10. Preferably, the fatty acids are linear and saturated. In some embodiments, suitable fatty acid detergent is sodium caprylate or a similar salt of caprylic acid. As described herein, the addition of caprylate (sodium caprylate) (C8) at neutral pH has been shown to improve protein recovery and prevents protein aggregation or nonspecific binding. In certain embodiments, the final concentration of caprylate acid solution comprising a protein or proteins of interest (such as antibodies or fragments thereof, antigens, therapeutic proteins, toxins, peptides, etc.) has a suitable concentration of detergent is between 25 mM and 300 mM, preferred between 50 mM and 250 mM, particularly preferred between 75 mM and 200 mM. The concentration might be about 25 mM, about 50 mM, about 75 mM, about 100 mM, about 125 mM, about 150 mM, about 175 mM, 200 mM about 250 mM or about 300 mM, depending on the ion exchange resin or chromatography conditions. A skilled person in the art will be able determine the most suitable fatty acid detergent and empirically elucidate the concentration of fatty acid detergents to make a solution. For example, it is known that carboxylic acid detergents having lower carbon chains will have less detergent characteristics, while higher carbon chains will have reduced solubility. Typically, higher detergent concentration is seen as providing a more robust process across different strains of influenza, due to disruption of any hydrophobic interactions and higher reduction of impurities as illustrated in FIG. 2. However, it is important that the amount of fatty acid detergents be present in an amount and at a pH to prevent precipitation of the proteins and residual DNA in solution.

In another aspect, the pH of the solution comprising proteins is maintained at a pH at which no (or an insignificant amount of) precipitation occurs of the proteins, nucleoproteins and residual DNA. For example, for caprylic acid, this is neutral pH. The optimum pH required to prevent protein precipitation can readily be determined empirically by the skilled person in the art. Preferably, the final pH of the mixture should be maintained to be between about 7.0 and 9.0. In some embodiments, the final pH of the mixture is maintained between about 7.2 and 7.5, e.g., between about 7.2-7.4, between about 7.2-7.3, between about 7.3-7.5, between about 7.4-7.5. In some embodiments, the final pH of the mixture is maintained at greater than or equal to about 7 (such as between about 7-9, e.g., about 7.0, about 7.5, about 8.0, about 8.5, about 9.0, etc.). In some embodiments, the pH of the solution comprising the proteins, residual DNA and caprylate should not be reduced to about 6.0 or less (e.g., about 5, 4, and 3). The pH can be adjusted before and/or after the addition of an anionic detergent (e.g., caprylate) to the sample. In some embodiments, the pH of the mixture could be adjusted before the addition of an anionic detergent (e.g., caprylate). In general, any art-recognized acids or buffers can be used to alter or adjust the pH of a mixture, including, for example, phosphate- and tris-containing buffers.

The method of the present invention may also be applied to partially purified protein samples to further remove DNA or undesired impurities by contacting the mixture with an anionic detergent solution under conditions which prevent precipitation of the proteins in the mixture and passing the mixture through an ion exchange matrix. The methods of the invention effectively remove host cell DNA contaminants to a concentration of <10 ng DNA per dose as recommend by WHO for continuous cell lines and nucleoprotein to a concentration of less than 0.5 µg NP per 10 µg HA. In a particular aspect, the amount of nucleoprotein removed by the present invention is at least 10%, 15%, 20%, 25%, 30%, 35%, 40%, 50%, 60%, 70%, 80% and 90% as determined by SDS-PAGE.

The composition comprising proteins and residual DNA in a solution of an anionic detergent is further processed to recover the desired product. Residual DNA is better adsorbed on an anion exchange membrane in the presence of the anionic detergent. Surprisingly, influenza nucleoproteins are also captured on the anion exchange membrane as identified by the inventors by electrophoretic analysis of adsorption pools. The inventors identified that nucleoproteins run with the residual DNA when contacted with a solution of anionic detergent. This finding has not been shown before and results in an enriched influenza product which is substantially free of residual DNA.

Accordingly, after residual host cell contaminants are removed by treatment of the contaminant-containing sample (e.g., cell culture and clarified bulk mixtures) with an anionic detergent and subsequent purification step in accordance with the methods described herein, such sample can contain no more than about 10000 ng/mg (e.g., no more than about 10000, 5000, 1000, 500, 200, 100, 50, 25, or 10 ng/mg) of protein contaminants. In some embodiments, such protein contaminants include no more than about 10000 ng/mg nucleoproteins, e.g., no more than about 10000, 5000, 1000, 500, 200, 100, 50, 25, or 10 ng/mg nucleoproteins.

Thus, any influenza product which comprises residual DNA and nucleoprotein can be enriched for HA and NA proteins by contact with an anionic detergent solution and processed through an ion exchange matrix. The person skilled in the art will be able to apply the methods of the present invention to influenza products generated from cell culture or egg culture.

Chromatography

The present invention may be used in commercial scale processing techniques that utilize ion exchange chromatography to produce bulk quantities of the finished product. It is known that during large scale manufacturing, the effect of the binding affinity between the residual DNA and virus particles or viral proteins may be further compounded during the concentration of the virus particles because the DNA may become physically trapped during the aggregation of the virus particles. Once the DNA is bound specifically or nonspecifically to the virus, or otherwise entrapped by aggregates of the virus or proteins, the use of ion exchange matrices as described in the art becomes relatively ineffective as a means for efficiently removing the DNA. Accordingly, the present invention relates to a purification process to remove residual DNA by purification with an anionic detergent solution and/or a suitable concentration or ionic strength provided by a salt buffer over a chromatography matrix.

An anionic Q membrane chromatography capsule may comprise a Mustang Q membrane a chromatography capsule (available from Pall Corporation) or Sartobind Q (a strongly basic anion exchanger membrane, available from Sartorius Stedim Biotech GmbH). Any positively charged ligand attached to the solid phase suitable to form the anionic exchange resin can be used, such as quaternary amino groups. Commercially available anion exchange resins include DEAE cellulose, POROS. PI 20, PI 50, HQ 10, HQ 20, HQ 50, D 50 from Applied Biosystems, SARTOBIND. Q from Sartorius, MONO Q, MINI Q, Source 15Q and 30Q, Q, DEAE and ANX SEPHAROSE. FAST FLOW, Q SEPHAROSE high Performance, QAE SEPHADEX. and FAST Q SEPHAROSE (GE Healthcare), WP PEI, WP DEAM, WP QUAT from J. T. Baker, HYDROCELL DEAE and HYDROCELL QA from BioChrom Labs Inc., UNOSPHERE Q, MACRO-PREP DEAE and MACRO-PREP High Q from Bio-Rad, Ceramic HyperD Q, ceramic HyperD DEAE, TRISACRYL M and LS DEAE, Spherodex LS DEAE, QMA SPHEROSIL LS, QMA SPHEROSIL M and MUSTANG Q from Pall Technologies, DOWEX Fine Mesh Strong Base Type I and Type II Anion Resins and DOWEX MONOSPHERE 77, weak base anion from Dow Liquid Separations, INTERCEPT Q membrane, MATREX CELLUFINE A200, A500, Q500, and Q800, from Millipore, FRACTOGEL EMD TMAE, FRACTOGEL. EMD DEAE and FRACTOGEL EMD DMAE from EMD, AMBERLITE weak strong anion exchangers type I and II, DOWEX weak and strong anion exchangers type I and II, DIAION weak and strong anion exchangers type I and II, DUOLITE from Sigma-Aldrich, TSKgel Q and DEAE 5PW and 5PW-HR, TOYOPEARL SUPERQ-650S, 650M and 650C, QAE- 550C and 650S, DEAE-650M and 650C from Tosoh, QA52, DE23, DE32, DE51, DE52, DE53, EXPRESS-Ion D and EXPRESS-Ion Q from Whatman.

Chromatographic separation over the ion exchange matrix is operated in flow-through mode. The specific methods used for the chromatography capture step, including flow of the sample through the column, wash, and elution, depend on the specific column and resin used and are typically provided by the manufacturers or are known in the art.

In an alternative aspect, modulation of ionic strength may also be employed during the chromatography step. The ionic strength of buffer solution may be determined from both molar concentration and charge numbers of all the ions present in the solution. The ionic strength, I, may be calculated using following formula:

$$I = \frac{1}{2}\sum_{i=1}^{n} c_i z_i^2$$

where $c_i$ is the molar concentration of ion i (mol·dm$^{-3}$), $z^i$ is the charge number of that ion, and the sum is taken over all ions in the solution. Generally a 1:1 electrolyte such as NaCl, the ionic strength is equal to its molar concentration, while multivalent ions contribute more to the ionic strength in the solution, for example, the ionic strength of the 2:2 electrolyte $MgSO_4$ is four times that of NaCl.

The preferred ionic strength will optimize the balance between removing the unwanted residual DNA while maintaining a high viral or protein yield that retains the antigenicity of the virus in a cost effective manner.

The person skilled in art will be able to design a chromatographic separation program depending on, for example, sample characteristics, chromatograph matrix properties and efficiency of fractionation. A saline buffer is preferably provided at or near a neutral pH such as about 7.0. 7.1, 7.2, 7.3, 7.4, 7.5, 7.6, 7.7 and 7.8. The pH should not be reduced below about 6 as the proteins of interest may lose their activity, aggregate or precipitate in the presence of an anionic detergent (e.g., fatty acid detergents). Suitable concentrations of buffer (e.g., sodium chloride buffer) may be between about 100 mM and 1M, such as 100 mM, 150 mM, 200 mM, 300 mM, 400 mM, 500 mM, 600 mM, 700 mM, 800 mM, 900 mM, and 1M. The optimum salt concentration depends on the ion exchange chromatography resin that is used. The person skilled in the art can easily determine the optimum salt concentration by routine test. For a TMAE resin the best sodium chloride concentration is about 300 mM, for SARTOBIND Q it is greater than 400 mM (for the use of caprylate as detergent; see Examples below).

As used herein the term "chromatography" refers to the process by which a solute of interest, e.g., a protein of interest, in a mixture is separated from other solutes in the mixture by percolation of the mixture through an adsorbent, which adsorbs or retains a solute more or less strongly due to properties of the solute, such as pI, hydrophobicity, size and structure, under particular buffering conditions of the process. In a method of the present invention, chromatography can be used to remove contaminants after the precipitate is removed from a mixture, including without limitation, a cell culture or clarified cell culture supernatant.

The term "impurities" as used herein generally refers to residual host cell DNA, empty viral particles, aggregated proteins or matter other than the intended component(s) of a product.

"Processing" or "processed" used in the context of the invention refers to a downstream step or steps performed after clarification or the initial starting materials comprising cellular byproduct and debris, colloidal particulates, large biomass and high cell densities. Techniques used in processing steps include isolation, purification, concentration, centrifugation, filtration, formulation, inactivation, splitting and various analytical operations performed for sterile biological products. "Processed" also may describe the steps of flowing or passing a sample through a chromatography column, resin, membrane, filter, or other mechanism, and can include a continuous flow through each mechanism as well as a flow that is paused or stopped between each mechanism.

Absent explicit teaching, a process comprising a step of mixing two or more components does not require any specific order of mixing. Thus, components can be mixed in any order. Where there are three components then two components can be combined with each other, and then the combination may be combined with the third component, etc.

The phrase "ion exchange material" refers to a solid phase that is negatively charged (e.g., a cation exchange resin) or positively charged (e.g., an anion exchange resin). In one embodiment, the charge can be provided by attaching one or more charged ligands (or adsorbents) to the solid phase, e.g., by covalent linking. Alternatively, or in addition, the charge can be an inherent property of the solid phase (e.g., as is the case for silica, which has an overall negative charge).

Accordingly, the present invention encompasses, but is not limited to, the following embodiments:

1. A method comprising a step of subjecting a first solution containing a protein of interest and an anionic detergent to an ion exchange matrix under a non-precipitating condition, so as to obtain a second solution containing the protein of interest, wherein the second solution contains less residual cellular contaminants than the first solution.
2. The method of embodiment 1, wherein the first solution is selected from the group consisting of: cell or tissue lysates, culture media, cell culture supernatants, plasma, and partially purified protein solutions.
3. The method of any one of the preceding embodiments, wherein the protein of interest is selected from the group consisting of: therapeutic proteins, immunogenic proteins (e.g., viral antigens), and antibodies or antigen-binding fragments thereof.
4. The method of any one of the preceding embodiments, wherein the anionic detergent is selected from the group consisting of: fatty acid detergents.
5. The method of any one of the preceding embodiments, wherein the anionic detergent is different from any other detergent used in a process of protein purification.
6. The method of any one of the preceding embodiments, wherein the anionic detergent does not include deoxycholate and/or sodium lauryl sulfate.
7. The method of any one of the preceding embodiments, wherein the ion exchange matrix comprises a basic anion exchanger membrane.
8. The method of any one of the preceding embodiments, wherein the non-precipitating condition comprises at or near neutral pH.
9. The method of any one of the preceding embodiments, wherein the second solution is an eluate.
10. The method of any one of the preceding embodiments, further comprising a step of further purification.
11. The method of any one of the preceding embodiments, further comprising a step of carrying out sterile filtration.

12. The method of any one of the preceding embodiments, further comprising a step of formulating the protein of interest into a pharmaceutical composition.
13. The method of any one of the preceding embodiments, further comprising a step of carrying out sterile filtration.
14. The method of embodiment 12 or 13, wherein the pharmaceutical composition is a prophylactic composition, therapeutic composition, or combination thereof.
15. The method of any one of embodiments 12-14, wherein the pharmaceutical composition further comprises a pharmaceutically acceptable excipient.
16. The method of any one of embodiments 12-15, wherein the pharmaceutical composition further comprises and adjuvant.
17. The method of any one of embodiments 12-16, further comprising a step of packaging the pharmaceutical composition into a sterile closed system.
18. The method of embodiment 17, wherein the sterile closed system is selected from the group consisting of: vials, syringes, and containers.
19. The method of embodiment 17 or 18, wherein the sterile closed system is plastic or glass.
20. The method of any one of embodiments 17-19, wherein the sterile closed system comprises a siliconized surface.
21. A use of the pharmaceutical composition of any one of embodiments 12-20, for the manufacture of a medicament for administering a subject in need thereof.
22. The pharmaceutical composition of any one of embodiments 12-20 for use as a medicament for administering to a subject.
23. A method comprising administering to a subject the pharmaceutical composition of any one of embodiments 12-20.
24. A viral vaccine comprising no more than 5 ng of residual DNA and no more than 1.0 µg nucleoprotein per dose.
25. The viral vaccine of embodiment 24, comprising no more than 1 ng of residual DNA and no more than 0.5 µg nucleoprotein per dose.
26. The viral vaccine of embodiment 24, comprising no more than 1 ng of residual DNA and no more than 0.1 µg nucleoprotein per dose.
27. The viral vaccine of any one of embodiments 24-26, wherein the viral vaccine is an influenza vaccine.
28. The viral vaccine of any one of embodiments 24-27, further comprising an adjuvant.
29. The viral vaccine of embodiment 28, wherein the adjuvant is selected from the group consisting of: alum adjuvants, oil-in-water adjuvants, virosomes and Toll-like receptor (TLR) agonists.

This invention is further illustrated by the following examples, which should not be construed as limiting.

EXAMPLES

An H5N1 virus was propagated in MDCK suspension cells, harvested and processed as described in Onions et al., 2010. The split virus preparation was subjected to ion exchange chromatography using a SARTOBIND Q (Sartorius) or a FRACTOGEL TMAE (EMD Millipore) membrane. The optimal salt concentration found for TMAE was determined to be approximately 300 mM, while the optimal concentration found for SARTOBIND Q was greater than 400 mM. Preparations with different detergents and chatoropric reagents were conducted. The pH of the final compositions was 7.5, except for the arginine compositions, which had a pH of 7.2. DNA reduction was assessed by Picogreen and protein yield was assessed by the BCA assay. Overall, SARTOBINDQ performed better than TMAE in DNA reduction; however, all runs utilizing sodium caprylate showed significant increase in DNA reduction compared to just NaCl. Robust results could be obtained with 50 mM caprylate and 400 mM NaCl on a SARTOBINDQ membrane. BCA values for the arginine might not be exact due to interference of arginine with the BCA assay. Arginine was not further investigated for yield due to insufficiently removing DNA. BCA and DNA data for these conditions are shown in FIGS. 3 and 4.

Samples from the following three runs were further examined by RP-HPLC for HA content: (i) Control—50 mM phosphate, 300 mM NaCl, pH 7.5; (ii) 50 mM phosphate, 100 mM sodium caprylate, 200 mM NaCl, pH 7.5; (iii) 50 mM phosphate, 100 mM sodium caprylate, 500 mM NaCl, pH 7.5. These runs were considered to be the best case for the conditions examined. Higher caprylate concentration is seen as providing a more robust process across strains based on the idea that a higher concentration of caprylate would more effectively disrupt any hydrophobic interactions and overall lead to a higher reduction of impurities. The yields by RP-HPLC were calculated and plotted in FIG. 1.

Material from these three runs was also analyzed by SDS-PAGE and can be seen in FIG. 2. The samples required sample prep prior to running on gels due to low protein concentration. The samples were concentrated 2.5 fold to ensure protein concentrations high enough to be visualized by SDS-PAGE. The samples were concentrated using a 15 mL Amicon ULTRA SPIN Tub with 10,000 MWCO membrane. The adsorption pool was also diluted in buffer and concentrated 2.5 fold to ensure that low molecular weight contaminants were not lost during the concentration process. This is demonstrated by comparing lanes labeled Adsorption and Adsorption, Concentrated. A dramatic difference in purity can be seen by comparing the control runs and the runs containing caprylate. The nucleoprotein in the caprylate runs is significantly diminished compared to runs just utilizing NaCl to optimize yield performance.

These experiments have successfully shown that secondary interactions, likely hydrophobic in nature, are playing a role in the diminished ability of AEX chromatography to adsorb the negatively charged impurity DNA. Without wishing to be bound by theory, the addition of caprylate to the adsorption pool likely disrupts this hydrophobic interaction and allows the binding of DNA and Nucleoprotein to the membrane or resin.

It should be understood that the invention has been described by way of example only and modifications may be made whilst remaining within the scope and spirit of the invention.

The various features and embodiments of the present invention, referred to in individual sections above apply, as appropriate, to other sections, mutatis mutandis. Consequently features specified in one section may be combined with features specified in other sections, as appropriate.

Throughout the specification, including the claims, where the context permits, the term "comprising" and variants thereof such as "comprises" or "comprising" are to be interpreted as including the stated element (e.g., integer) or elements (e.g., integers) without necessarily excluding any other elements (e.g., integers).

Those skilled in the art will recognize, or be able to ascertain using no more than routine experimentation, many equivalents to the specific embodiments of the invention described herein. Such equivalents are intended to be encompassed by the following claims.

We claim:

1. A method for removing Influenza Nuclear Protein (NP) from a preparation comprising virus proteins of interest, the method comprising the steps of:

a. splitting a virus preparation derived from cell culture or eggs, b. adding an anionic detergent to the virus preparation under non-precipitating conditions whereby no substantial precipitation of viral proteins or DNA occurs, and c. processing the virus preparation through an ion exchange matrix, whereby the nuclear protein is bound to the ion exchange matrix, wherein the anionic detergent is not deoxycholate, sodium lauryl sulfate, or a combination thereof, and wherein the pH of the mixture of the virus preparation and the anionic detergent is between about 7.0 to about 9.0.

2. The method of claim 1, further comprising a clarification step.

3. The method of claim 1, further comprising a concentration step.

4. The method of claim 1, further comprising a depth filtration step.

5. The method of claim 1, further comprising an inactivation step prior to the ion exchange step.

6. The method of claim 5, wherein the inactivation step comprises inactivation with betapropiolactone.

7. The method of claim 1, wherein the anionic detergent is not the same as other detergents used in the process.

8. The method of claim 1, wherein the anionic detergent is a fatty acid detergent.

9. The method of claim 1, wherein the anionic detergent is a carboxylic acid detergent which comprise 4-10 carbon atoms in length.

10. The method of claim 9, wherein the carboxylic acid detergent is selected from the group consisting of caprylic (8) acid, valeric (5) acid, caproic (6) acid, enanthic (7) acid, pelargonic (9) acid, and capric (10) acid.

11. The method of claim 10, wherein the carboxylic acid is caprylic acid.

12. The method of claim 11, wherein the caprylic acid is sodium caprylate.

13. The method of claim 1, wherein the anionic detergent is present at a concentration of 25 nM-500 nM.

14. The method of claim 1, wherein the ion exchange resin is a strongly basic anion exchanger membrane.

15. The method of claim 1, wherein the ion exchange resin is a cross-linked polymethacrylate cation exchanger membrane.

16. The method of claim 1, wherein virus proteins of interest comprise influenza hemagglutinin (HA).

17. A method for removing Influenza Nuclear Protein (NP) from a preparation comprising virus proteins of interest, the method comprising the steps of:

a. splitting a virus preparation derived from cell culture or eggs, b. adding a fatty acid anionic detergent to the virus preparation and maintaining the pH of the mixture is between about 7.0 to about 9.0, whereby no substantial precipitation of viral proteins or DNA occurs, and c. processing the virus preparation through an ion exchange matrix, whereby the nuclear protein is bound to the ion exchange matrix.

18. The method of claim 17, wherein the anionic detergent is a carboxylic acid detergent which comprise 4-10 carbon atoms in length.

19. The method of claim 17, wherein the carboxylic acid detergent is selected from the group consisting of caprylic acid, valeric acid, caproic acid, enanthic acid, pelargonic acid, and capric acid.

20. The method of claim 10, wherein the carboxylic acid is caprylic acid.

* * * * *